(12) United States Patent  (10) Patent No.: US 7,731,914 B2
Ivansons et al.  (45) Date of Patent: Jun. 8, 2010

(54) OZONE INFECTION CONTROL DEVICE

(75) Inventors: Ivars V. Ivansons, Elkton, MD (US);
Dudley W. C. Spencer, Wilmington, DE (US)

(73) Assignee: Denco, Inc., Wilmington, DE (US)

( * ) Notice: Subject to any disclaimer, the term of this patent is extended or adjusted under 35 U.S.C. 154(b) by 519 days.

(21) Appl. No.: 11/775,906

(22) Filed: Jul. 11, 2007

(65) Prior Publication Data

US 2009/0016942 A1   Jan. 15, 2009

(51) Int. Cl.
*B01J 19/08* (2006.01)

(52) U.S. Cl. ............................. 422/186.04; 422/186.12; 604/25

(58) Field of Classification Search ............ 422/186.04, 422/186.12; 604/25
See application file for complete search history.

(56) References Cited

U.S. PATENT DOCUMENTS

| | | | |
|---|---|---|---|
| 4,610,670 A | 9/1986 | Spencer | |
| 4,619,642 A | 10/1986 | Spencer | |
| 4,770,735 A | 9/1988 | Shaposka | |
| 4,793,880 A | 12/1988 | Shaposka | |
| 4,832,773 A | 5/1989 | Shaposka | |
| 4,864,101 A | 9/1989 | Shaposka | |
| 4,897,138 A | 1/1990 | Shaposka | |
| 4,913,756 A | 4/1990 | Shaposka | |
| 4,933,036 A | 6/1990 | Shaposka | |
| 5,141,592 A | 8/1992 | Shaposka | |
| 5,156,701 A | 10/1992 | Spencer | |
| 5,158,630 A | 10/1992 | Shaposka | |
| 5,209,800 A | 5/1993 | Spencer | |
| 5,244,522 A | 9/1993 | Spencer | |
| 5,248,359 A | 9/1993 | Shaposka | |
| 5,256,229 A | 10/1993 | Spencer | |
| 5,279,685 A | 1/1994 | Ivansons | |
| 5,397,425 A | 3/1995 | Ivansons | |
| 5,525,186 A | 6/1996 | Ivansons | |
| 5,632,852 A | 5/1997 | Ivansons | |
| 5,674,333 A | 10/1997 | Spencer | |
| 5,855,731 A | 1/1999 | Spencer | |
| 5,871,612 A | 2/1999 | Spencer | |
| 5,911,957 A * | 6/1999 | Khatchatrian et al. | .. 422/186.07 |
| 6,020,574 A | 2/2000 | Ivansons | |
| 6,177,652 B1 | 1/2001 | Ivansons | |
| 6,637,489 B1 | 10/2003 | Spencer | |
| 7,398,813 B2 | 7/2008 | Ivansons | |
| 2003/0065292 A1* | 4/2003 | Darouiche et al. | .......... 604/265 |

\* cited by examiner

*Primary Examiner*—Kishor Mayekar
(74) *Attorney, Agent, or Firm*—Connolly Bove Lodge & Hutz

(57) ABSTRACT

An infection control device includes a plurality of air inlets spaced around the device's peripheral skirt. A negative ion ozone generator having a plurality of spaced pointed projections is inwardly of the peripheral skirt with a ground disk inwardly of the generator. Air flows through the inlets to the generator, to the disk and to a catheter exit site.

19 Claims, 4 Drawing Sheets

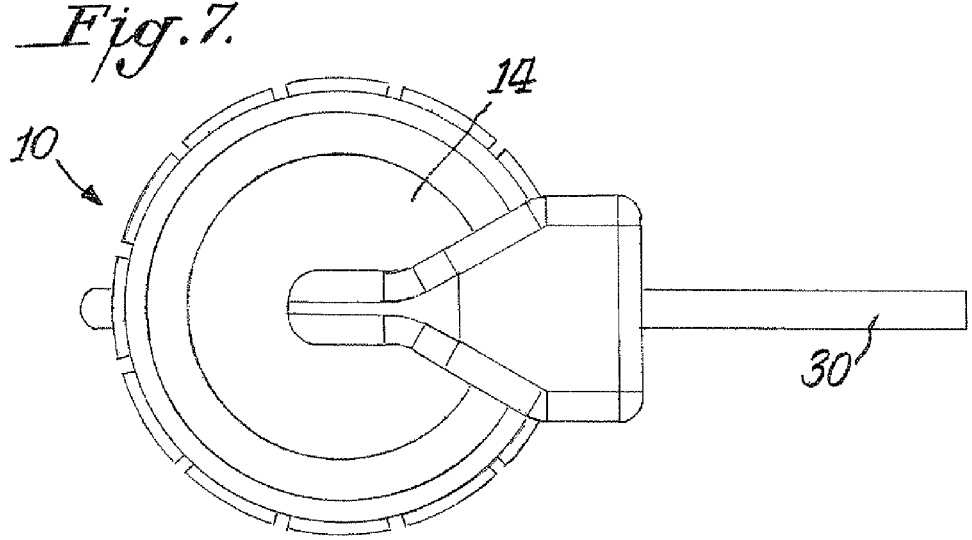
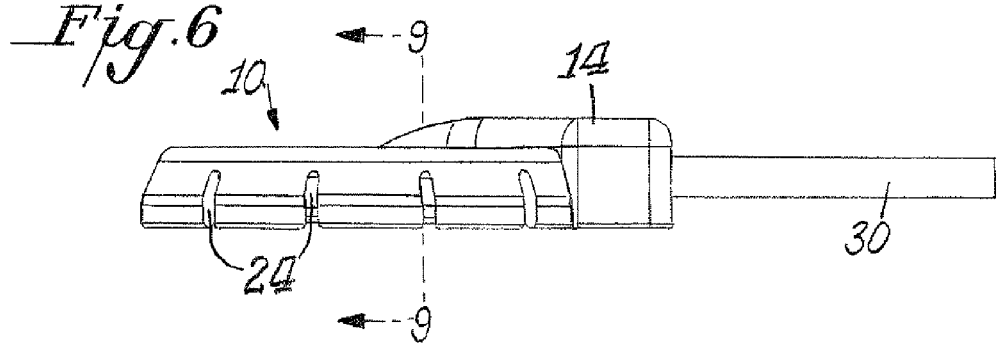
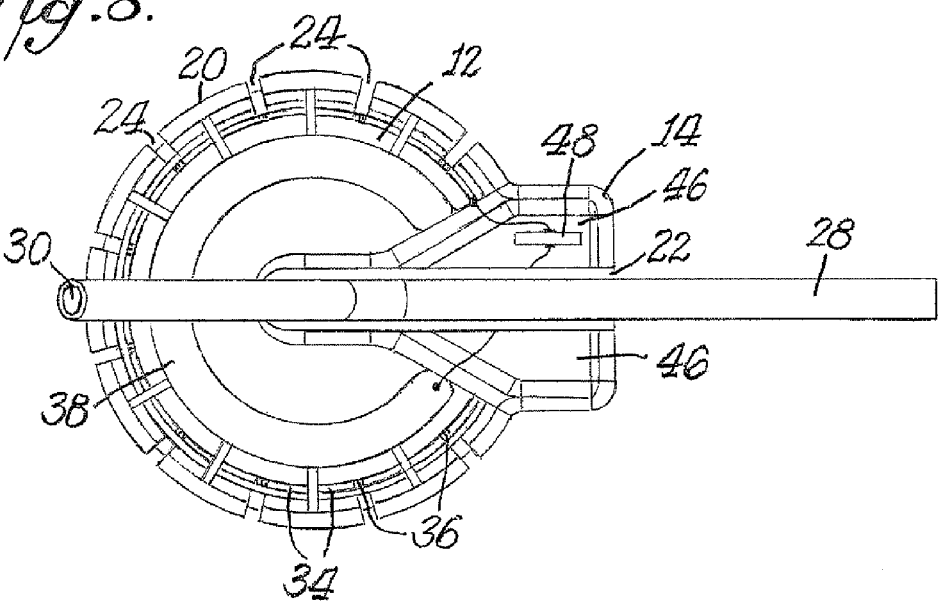

__US 7,731,914 B2__

OZONE INFECTION CONTROL DEVICE

BACKGROUND OF THE INVENTION

Various medical practices include inserting a catheter into and below the skin of the patient. If proper care is not taken microorganisms result at the operative site. For example, common bacteria associated with peritoneal catheters include staph aureus, pseudomonas aeruginosa and staph epidermidis. Airborne bacterial such as acinetobacter might also be at the site. It would be desirable if some form of infection control device could be provided in conjunction with the catheter to minimize dangers resulting from such microorganisms.

U.S. Pat. No. 5,632,852 discloses an ion generator as part of a connect/disconnect device for plastic tubes. As disclosed therein when plastic tubes are melted in a connect or disconnect procedure aerosol particles are formed. The aerosol particles are confined or contained by providing an ion generator which imparts an electrical charge to the particles. The charged particles are then collected by a collector plate within the device.

SUMMARY OF THE INVENTION

An object of this invention is to provide an infection control device which utilizes ozone converted from oxygen in air as the control mechanism.

A further object of this invention is to provide such an ozone infection control process and device which may include structure for holding the catheter itself as well as structure for generating the ozone and controlling its flow to bathe the catheter at the exit site with an ozone/oxygen mixture.

In accordance with this embodiment, an ozone infection control system includes a body portion having a passageway or channel for receiving a catheter. The body portion has a downwardly extending periphery skirt which includes a plurality of air inlet openings spaced around the skirt. A negative ion ozone generator is provided in the body and utilizes a plurality of spaced projections inwardly of the skirt in the path of motion of the air flowing through the inlet openings to generator ozone from the air. A ground disk is mounted within the body portion inwardly of the ozone generator. The path of air extends from the inlet openings to the ozone generator and then to the ground disk and then exits at the catheter passageway to bathe the catheter with antimicrobial ozone at the catheter exit site.

In a preferred practice of this invention the ozone generator is in the form of ring mounted below, but to the top of the body portion. The projections are pointed spikes located at the airflow inlets. The ground disk is preferably a plate mounted inwardly of and below the ozone generator ring. The catheter passageway is a channel centrally located in the body member above the ground disk.

The inventive system may also be practiced where catheters are not used, particularly in non-chronic applications.

THE DRAWINGS

FIG. 6 is a side elevational view of the device shown in FIGS. 2-5;

FIG. 7 is a top plan view of the device shown in FIGS. 2-6;

FIG. 8 is a bottom plan view of the device shown in FIGS. 2-7;

DETAILED DESCRIPTION

Figure 1:
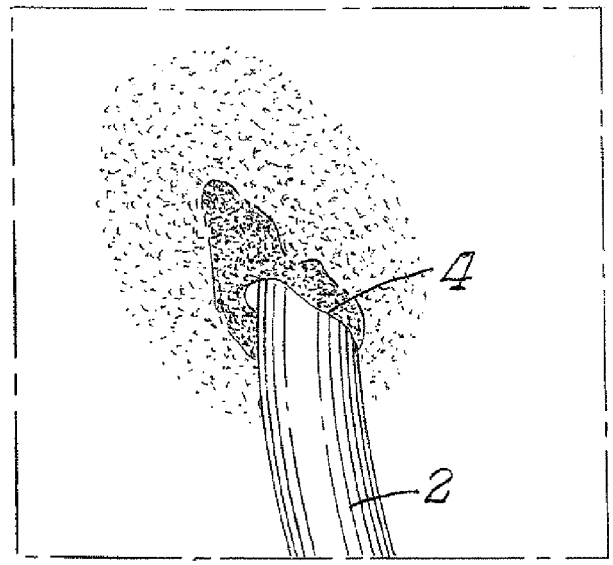
FIG. 1 is a perspective view showing the exit site of a catheter which does not include the benefits of this invention.
Figure 2:
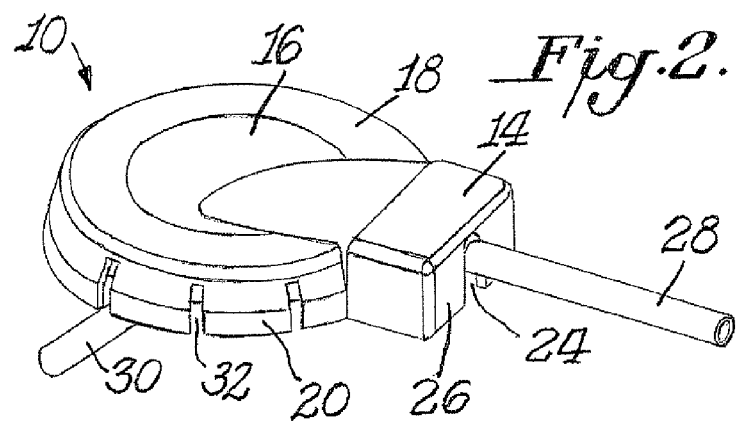
FIG. 2 is a top perspective view of an ozone infection control device in accordance with this invention.
Figure 3:
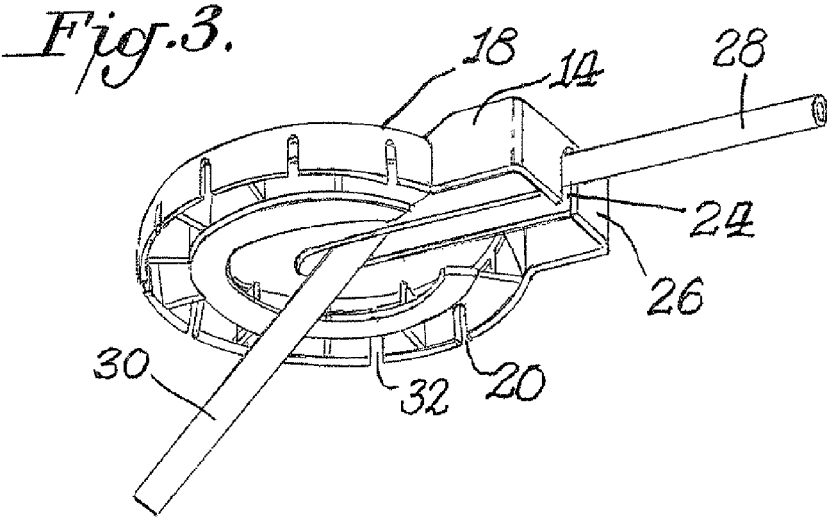
FIG. 3 is a bottom perspective view of the device shown in FIG. 2.

The present invention is directed to preventing various microorganisms, as previously described, from causing, for example, pain and discomfort at the exit site of a catheter. FIG. 1 shows an exit site which does not include the benefits of this invention. As shown therein, a catheter 2 extends outwardly from the exit site or opening 4 in the skin. Because of the presence of various types of microorganisms the exit site is characterized by pain/tenderness, by discolor, by crust, by a scab, by drainage, by swelling, by granulation tissue and by tunnel involvement.

FIGS. 2-9 illustrate an ozone infection control device 10 in accordance with this invention. As shown therein, device 10 includes a body portion 12 in the form of a top outer peripheral wall 18 which merges into a downwardly dished area 16. See FIG. 9. Upwardly extending top wall 18 terminates in a downwardly extending peripheral skirt 20.

As shown in the various figures the body portion 12 contains a fan shaped catheter housing 14 extending outwardly from the central portion or area of body portion 12. Catheter housing 14 includes a passageway or channel 22 (FIG. 8) extending from a slot 24 in a lateral wall 26 of catheter housing 14. See FIG. 3. The passageway 22 may simply be a channel or slot for receiving the catheter and is preferably dimensioned to snugly receive the plastic tube or catheter 28 which extends along the outside of the patient's skin and enters the device 10 through inlet slot 24. The lower surface of skirt 20 is placed against the skin of the patient. Catheter 28 is then bent downwardly at the central portion of device 10 to form a downwardly extending catheter portion 30 which would be located in the patient's body at the exit site of the catheter. Such catheter could be used for various purposes, such as being a peritoneal catheter.

The housing 14 may also function as a power housing for the necessary electronics or batteries used for powering device 10, as later described.

As shown in FIG. 8 the catheter housing 14 extends from the central portion of body portion 12 to at least and preferably beyond the peripheral skirt 20. Catheter housing 14 includes a channel or slot 22 for receiving the horizontal portion 28 of the catheter and for receiving at the central portion of device 10 the generally vertical portion 30 of the catheter which is located at the catheter exit and extends into the body of the patient. The catheter housing 14 also includes chambers 46,46 which may house the electronics 48 (shown in FIG. 10) and the power source, such as batteries for the electronics.

As illustrated in the various figures a series or plurality of air inlet openings or slots 32 is arranged preferably equally spaced around the peripheral skirt except in the area of boss 14 and its lateral wall 26.

Figure 4:
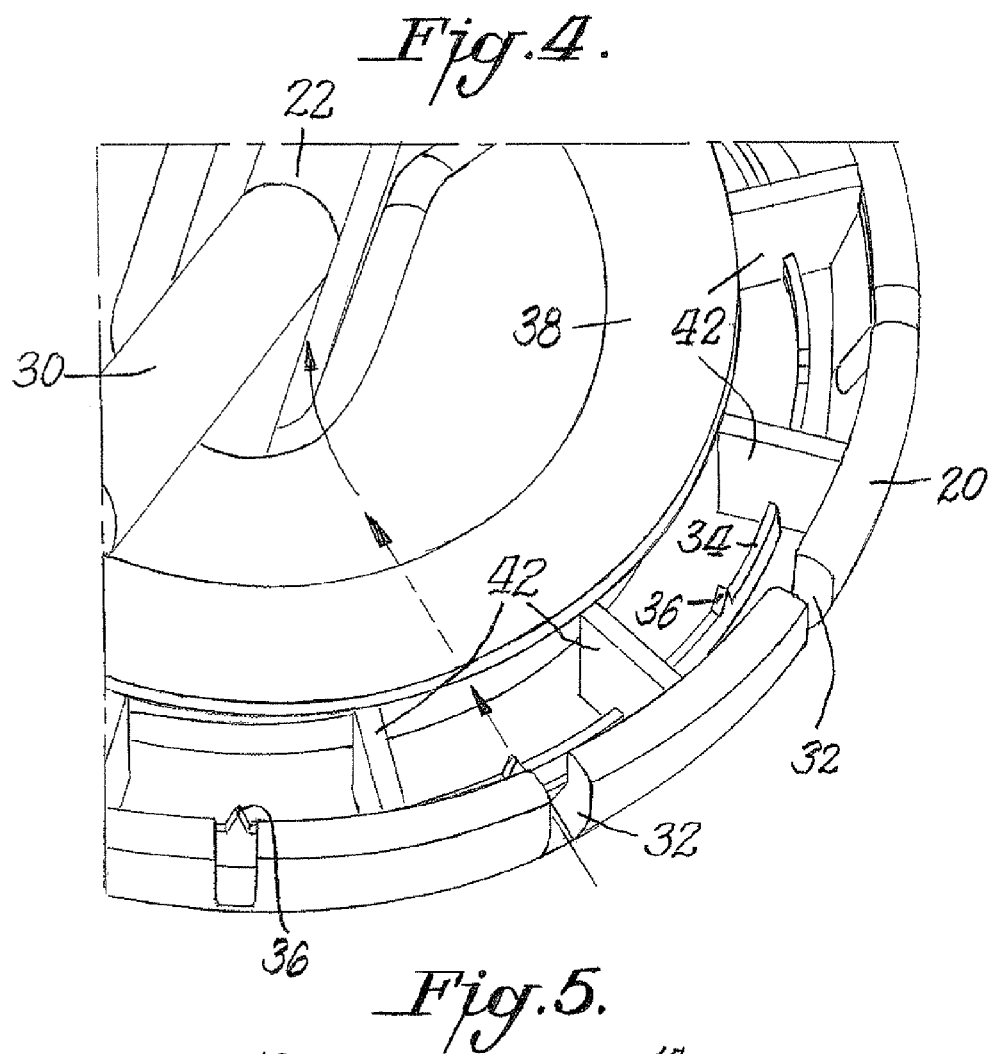
FIG. 4 is a bottom view of a portion of the device shown in FIGS. 2-3.
Figure 5:
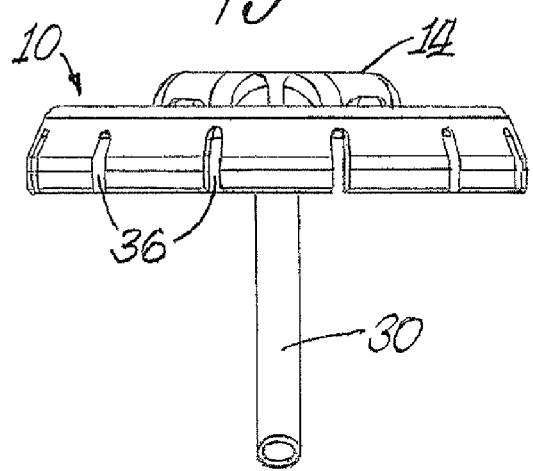
FIG. 5 is a front elevational view of the device shown in FIGS. 2-4.
Figure 9:
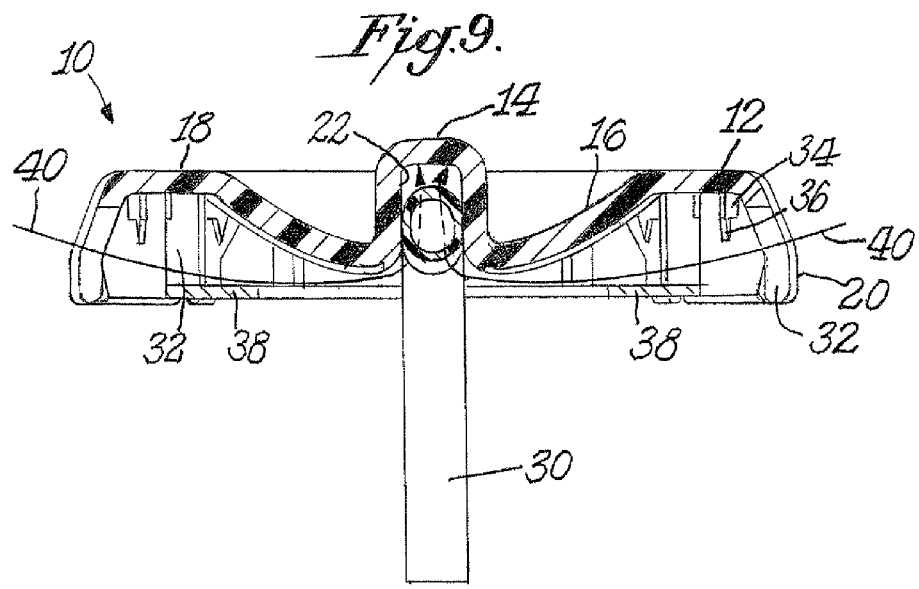
FIG. 9 is a cross-sectional view taken through FIG. 6 along the line 9-9.

As best shown in FIGS. 4, 8 and 9 a negative ion ozone generator 34 is mounted in body portion 12 inwardly of skirt 20. Generator 34 includes a plurality of downwardly extending projections 36 preferably in the form of pointed spikes. Preferably the number of spikes 36 corresponds to the number of inlet slots 32 with each spike located at a respective inlet slot. Thus, air entering the body portion through inlet openings or slots 32 follows a path directed to the projections or spikes 36 of ozone generator 34. Ozone generator 34 functions as a negative ion probe to convert the oxygen in the air to ozone.

As best illustrated in FIG. 9 ozone generator 34 is located at and below the upper wall 18 of body portion 12 with the projections or spikes 36 extending downwardly. The air inlet slots 24 extend upwardly from the lower surface of skirt 20 to a sufficient extent that the slots are located in line with spikes 36.

As shown in FIGS. 4 and 9, a positively charged ground disk 38 is located within body portion 12 of device 10 inwardly of ozone generator 34. Ground disk 38 is in the form of a flat annular O-shaped plate generally concentric with the ring-shaped ozone generator 34. As illustrated in FIG. 9 ground plane disk 38 is located near the lower edge of the peripheral skirt 20. By having a downwardly dished portion 16 of body member 12, an air flow path is created which is shown in FIG. 9 by the arrows 40 wherein the air flows into the device 10 through the inlet opening slots 32 to the ozone generator 34 where the projections 36 convert the oxygen to ozone. The path of flow then extends downwardly between dished portion 16 and ground disk 38 and finally into the channel 22 or passageway for receiving the catheter so that ionized air bathes the catheter exit site with antimicrobial ozone which would exit at the catheter through slot 24 at the end of channel 22.

As illustrated in FIG. 4 a series of ribs or webs 42 interconnect the ground disk 38 with the ozone generator 34. The webs 42 extend to the inner surface of skirt 20. A unit is thereby created comprising the ozone generator 34 and the ground disk 38 with the webs 42. This unit could be periodically removed for repair or replacement purposes. By having the webs extend beyond the ozone generator 34 to the peripheral skirt 20 there is assurance of properly locating the ozone generator and the ground disk with respect to each other and with respect to the air inlet slots 32.

A further advantage of webs or ribs 42 is that the webs form channels to also confine the flow of air along its desired path.

Figure 10:
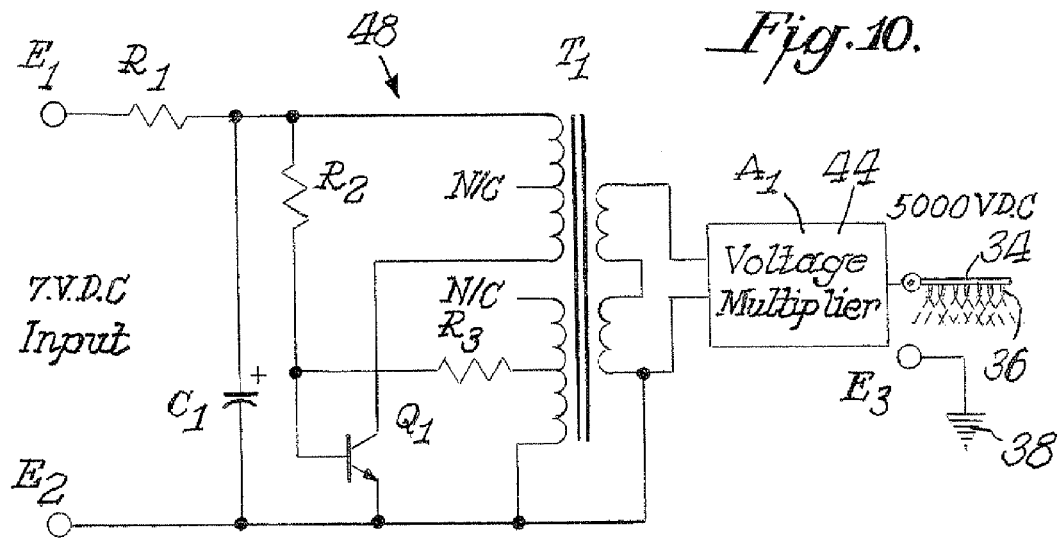
FIG. 10 is an electrical wiring diagram which may be used in the device of FIGS. 2-9.

FIG. 10 illustrates circuitry that could be used for powering device 10. Such circuitry could be based upon the type of circuitry disclosed in U.S. Pat. No. 5,632,852, all of the details of which are incorporated herein for all purposes.

In a practice of the invention the ozone could be generated at projections or pointed spikes 36 by the application of 5,000-7,000 volts. If desired, a cover or seal could be provided at the bottom of skirt 20 such as an elastic band or suitable bandage to firmly mount device 10 against the skin and thereby assure confining the airflow in its desired path. In addition, a belt could be mounted around the device 10 to assure its proper placement on the patient. Where a battery is used as the power in housing 14, such battery could be operated at 6-7 volts. A transformer/voltage multiplier 44 (FIG. 10) could increase the 6-7 volts battery voltage up to 1,000 times.

Any suitable number of inlet openings and projections could be used in the practice of this invention. Preferably, there would be 10 slots 32 and 10 projections 36.

Any suitable materials could be used. For example, the body portion or housing 12 could be made of any suitable plastic. Preferably, the ground plane disk 38 is made of a conductive material, such as stainless steel, to function as a positive or ground in conjunction with the negative polarity of ozone generator 34. Where plastic materials are used for forming the various parts of device 10 such parts could be injection molded. For example, a one piece mold would provide uniform thickness throughout.

By having the ozone generator 34 and ground disk 38 as part of a single unit with webs 42, it is easy to clean device 10 or to dispose of the unit and replace it with a similar unit. The unit would snap into place because of the dimensions and geometry conforming to the corresponding portions of body portion 12.

In use, catheter portion 30 would be inserted into the exit site of the patient. Device 10 would be mounted to the catheter at the exit site with the lower edge of the peripheral skirt 20 located against the skin of the patient around the catheter exit site. Any added structure such as belts, straps, bandages could be used to assure that device 10 remains in place. The circuitry would be actuated so that generator 34 functions to convert air flowing into the device 10 into ozone or ionized air which then travels through the device 10 to bathe the catheter exit site and then exit from the device 10 through the channel or passageway 24.

While the above description relates to one practice of this invention, the invention has broader application. In that regard, the invention may be considered as relating to a process and a contiguous device for ameliorating a patient suffering from pathogens of the Bacterial, Virus and Fungi genus. The process utilizes the pathogens weak spot of an extremely thin membrane of lipids. In previous disclosures, pathogen necrosis has been shown to occur when temperatures of 250° C. are attained and held for 20 milliseconds destroying the cells' lipid membrane. The same effect can be achieved by Ozone ($O_3$), in very small concentrations of gaseous ozone (<5%) in air destroying the pathogen's lipid wall without added heat.

The Ozone gas has virtually no shelf-life and must be used, as made. In this practice of the invention a device helps form a gaseous ozone shield over chronic skin afflictions including chronic skin punctures of indwelling catheters that are used for infusions, drains and other surgical protocols. Combining a process and device results in a combination of controlled ozone dosage and controlled distribution built into the device at manufacture.

The skin abrasions, cuts, burns and one time surgical procedures, oxygen in the air is a powerful healing agent. Healing, however, is reduced in effectiveness by having pathogens in the air deposit themselves in or near the lesion. This will not only slow healing, but will make healing difficult, particularly when pathogens that have become immune to antibiotics are present. By adding a small continuous well controlled dosage of ozone to the air over the wound site, a field/shield will be formed where pathogens will be reduced or eliminated, allowing the wounds to heal faster. This process is particularly helpful when the wound must heal around a movable foreign object as in indwelling dialysis and urinary catheter applications. Catheters are notorious for infections that develop at a rate of 10%/day and are becoming antibiotic tolerant. This condition can be stopped by the disclosed process and device.

In the above practices of the invention a device such as device 10 would be used but would not need to include any catheter. Instead the device 10 would be placed at the site where it is desired to produce the ozone for obtaining the above noted beneficial effects. The device would thereby create the controlled ozone/oxygen combination.

What is claimed is:

1. An ozone infection control device comprising a body portion having an exit passageway, said body portion having a downwardly extending peripheral skirt, a plurality of air inlet openings spaced around said peripheral skirt, a negative ion ozone generator having a plurality of spaced projections within said body portion spaced inwardly of said peripheral skirt in a path of flow of air flowing though said inlet openings to generate ozone from the air at said ozone generator, a ground disk within said body portion inwardly of said ozone generator, and the path of flow in said body portion extending from said inlet openings and to said ozone generator and then to said ground disk and then exiting at said exit passageway for bathing a site under said device with ozone.

2. The device of claim 1 wherein said ozone generator comprises a negatively charged ring having said plurality of spaced projections extending downwardly, said spaced projections terminating in points, and said ground disk being oppositely charged from said ozone generator and being in the form of an annular plate located inwardly of and below said ozone generator.

3. The device of claim 2 wherein said air inlet openings are slots extending through said peripheral skirt, said slots being arranged in an arc equally spaced from each other, said spaced projections being arranged co-arcuate to said inlet slots with each of said slots being in line with a respective one of said projections.

4. The device of claim 3 including a plurality of webs interconnecting said ground disk with said ozone generator ring.

5. The device of claim 4 wherein said webs extend to and are disposed against the inner surface of said peripheral skirt.

6. The device of claim 5 wherein said ground disk and said ozone generator ring and said webs form a unit which is removably mounted in said body portion.

7. The device of claim 6 wherein each of said webs is located between a set of adjacent inlet slots.

8. The device of claim 2 including a plurality of webs interconnecting said ground disk with said ozone generator ring.

9. The device of claim 8 wherein said webs extend to and are disposed against the inner surface of said peripheral skirt.

10. The device of claim 8 wherein said ground disk and said ozone generator ring and said webs form a unit which is removably mounted in said body portion.

11. The device of claim 2 wherein said body portion includes a top wall from which said peripheral skirt extends downwardly, said top wall being downwardly dished inwardly from said peripheral skirt toward a central area of said body portion, said downwardly dished top wall being located above and inwardly of said ground disk to create a flow path from said inlet slots below said ozone generator above said disk and to said central area of said body portion and said flow path then exiting from said body portion through said passageway.

12. The device of claim 11 wherein said body portion includes a catheter housing extending from said central area of said body portion outwardly beyond said peripheral skirt, and said passageway being a channel extending completely through said catheter housing from externally of said catheter housing to said central area of said body portion.

13. The device of claim 12 wherein said catheter housing includes at least one chamber for receiving electronics and a power source for said device.

14. The device of claim 4 wherein said body portion includes a top wall from which said peripheral skirt extends downwardly, said top wall being downwardly dished inwardly from said peripheral skirt toward a central area of said body portion, said downwardly dished top wall being located above and inwardly of said ground disk to create the flow path from said inlet slots below said ozone generator above said disk and to said central area of said body portion and said flow path then exiting from said body portion through said passageway.

15. The device of claim 14 wherein said exit passageway is shaped for receiving a catheter whereby the catheter is bathed at the operative site which would comprise a catheter exit site.

16. The device of claim 15 wherein said body portion includes a catheter housing extending from said central area of said body portion outwardly beyond said peripheral skirt, and said passageway being a channel extending completely through said catheter housing from externally of said catheter housing to said central area of said body portion.

17. The device of claim 16 wherein said catheter housing includes at least one chamber for receiving electronics and a power source for said device.

18. The device of claim 17 wherein said webs extend to and are disposed against the inner surface of said peripheral skirt.

19. The device of claim 18 wherein said ground disk and said ozone generator ring and said webs form a unit which is removably mounted in said body portion.

* * * * *